(12) United States Patent
Finke

(10) Patent No.: US 11,974,931 B2
(45) Date of Patent: May 7, 2024

(54) ENVELOPING BODY

(71) Applicant: OTTOBOCK SE & CO. KGAA, Duderstadt (DE)

(72) Inventor: Lars Benjamin Finke, Landolfshausen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 9 days.

(21) Appl. No.: 16/096,190

(22) PCT Filed: Apr. 25, 2017

(86) PCT No.: PCT/EP2017/059729
§ 371 (c)(1),
(2) Date: Oct. 24, 2018

(87) PCT Pub. No.: WO2017/186680
PCT Pub. Date: Nov. 2, 2017

(65) Prior Publication Data
US 2019/0117419 A1    Apr. 25, 2019

(30) Foreign Application Priority Data
Apr. 26, 2016 (DE) .......................... 102016107670.8

(51) Int. Cl.
*A61F 2/78* (2006.01)
*A41D 13/015* (2006.01)
(Continued)

(52) U.S. Cl.
CPC ........ *A61F 2/7843* (2013.01); *A41D 13/0155* (2013.01); *A41D 13/129* (2013.01);
(Continued)

(58) Field of Classification Search
CPC ............ A61F 2/7843; A61F 2002/7868; A61F 2002/7837; B29D 22/023
(Continued)

(56) References Cited

U.S. PATENT DOCUMENTS 1,057,562 A * 4/1913 Point ..................... A61F 2/7843
623/37
2,597,924 A   5/1952 Davenport et al.
(Continued)

FOREIGN PATENT DOCUMENTS

DE       837 293    * 4/1952 ............... A61F 2/74
DE       917687      9/1954
(Continued)

OTHER PUBLICATIONS

U.S. Appl. No. 62/426,712, filed Nov. 28, 2016.*
PCT International Search Report for PCT International Patent Application No. PCT/EP2017/059729, dated Jul. 17, 2017.

*Primary Examiner* — David H Willse
(74) *Attorney, Agent, or Firm* — HOLLAND & HART LLP

(57) ABSTRACT

An enveloping body for at least partly enveloping a limb, comprising an enclosed volume and a connection for supplying fluid to the volume and discharging it from the volume, wherein the enveloping body defines an inner circumference and an outer circumference, wherein the inner circumference of the enveloping body increases as the pressure of the volume increases.

18 Claims, 6 Drawing Sheets

(51) Int. Cl.
<table>
<tr><td>A41D 13/12</td><td>(2006.01)</td></tr>
<tr><td>A43B 3/24</td><td>(2006.01)</td></tr>
<tr><td>A43B 11/00</td><td>(2006.01)</td></tr>
<tr><td>A47G 25/80</td><td>(2006.01)</td></tr>
<tr><td>A47G 25/90</td><td>(2006.01)</td></tr>
<tr><td>A61F 2/74</td><td>(2006.01)</td></tr>
<tr><td>A61F 5/01</td><td>(2006.01)</td></tr>
<tr><td>A61F 5/058</td><td>(2006.01)</td></tr>
<tr><td>A43B 3/02</td><td>(2006.01)</td></tr>
<tr><td>A43B 3/26</td><td>(2006.01)</td></tr>
<tr><td>A43B 23/02</td><td>(2006.01)</td></tr>
<tr><td>A61F 2/50</td><td>(2006.01)</td></tr>
</table>

(52) U.S. Cl.
CPC .............. *A43B 3/248* (2013.01); *A47G 25/80* (2013.01); *A47G 25/905* (2013.01); *A61F 2/74* (2021.08); *A61F 2/7812* (2013.01); *A61F 5/01* (2013.01); *A61F 5/05816* (2013.01); *A41D 2400/44* (2013.01); *A43B 3/02* (2013.01); *A43B 3/24* (2013.01); *A43B 3/26* (2013.01); *A43B 11/00* (2013.01); *A43B 23/029* (2013.01); *A61F 2002/501* (2013.01); *A61F 2002/5032* (2013.01); *A61F 2002/7825* (2013.01); *A61F 2002/7837* (2013.01); *A61F 2002/7868* (2013.01)

(58) Field of Classification Search
USPC ...................................................... 623/37, 32
See application file for complete search history.

(56) References Cited

U.S. PATENT DOCUMENTS

<table>
<tr><td>2,634,424</td><td>A</td><td></td><td>4/1953</td><td>O'Gorman</td><td></td></tr>
<tr><td>4,128,903</td><td>A</td><td>*</td><td>12/1978</td><td>Marsh ....................... A61F 2/80</td><td></td></tr>
<tr><td></td><td></td><td></td><td></td><td></td><td>623/36</td></tr>
<tr><td>5,108,456</td><td>A</td><td></td><td>4/1992</td><td>Coonan, III</td><td></td></tr>
<tr><td>5,387,245</td><td>A</td><td></td><td>2/1995</td><td>Fay et al.</td><td></td></tr>
<tr><td>2003/0078674</td><td>A1</td><td></td><td>4/2003</td><td>Phillips</td><td></td></tr>
<tr><td>2006/0184083</td><td>A1</td><td>*</td><td>8/2006</td><td>Buckman ............ A61F 5/05816</td><td></td></tr>
<tr><td></td><td></td><td></td><td></td><td></td><td>602/32</td></tr>
<tr><td>2010/0121243</td><td>A1</td><td>*</td><td>5/2010</td><td>Aune, Jr. ............. A61H 1/0296</td><td></td></tr>
<tr><td></td><td></td><td></td><td></td><td></td><td>602/32</td></tr>
<tr><td>2013/0218296</td><td>A1</td><td></td><td>8/2013</td><td>Koniuk et al.</td><td></td></tr>
<tr><td>2016/0270479</td><td>A1</td><td></td><td>9/2016</td><td>Suzuki</td><td></td></tr>
<tr><td>2018/0146721</td><td>A1</td><td>*</td><td>5/2018</td><td>Aherne, III ........ A41D 13/0025</td><td></td></tr>
</table>

FOREIGN PATENT DOCUMENTS

<table>
<tr><td>DE</td><td>1008224</td><td></td><td>5/1957</td><td></td></tr>
<tr><td>EP</td><td>2327378 A1</td><td></td><td>6/2011</td><td></td></tr>
<tr><td>FR</td><td>1.035.755</td><td>*</td><td>4/1953</td><td>............... A61F 2/74</td></tr>
<tr><td>GB</td><td>2116432 A</td><td>*</td><td>9/1983</td><td>............... A61F 2/80</td></tr>
<tr><td>JP</td><td>H06296635 A</td><td>*</td><td>10/1994</td><td>............... A61F 5/01</td></tr>
<tr><td>JP</td><td>2009-112380 A</td><td>*</td><td>5/2009</td><td>............ A61F 13/04</td></tr>
<tr><td>SU</td><td>731963</td><td></td><td>5/1980</td><td></td></tr>
<tr><td>WO</td><td>WO 2015/083810 A1</td><td>*</td><td>6/2015</td><td>............. A43B 11/00</td></tr>
<tr><td>WO</td><td>2015083810 A1</td><td></td><td>3/2017</td><td></td></tr>
</table>

* cited by examiner

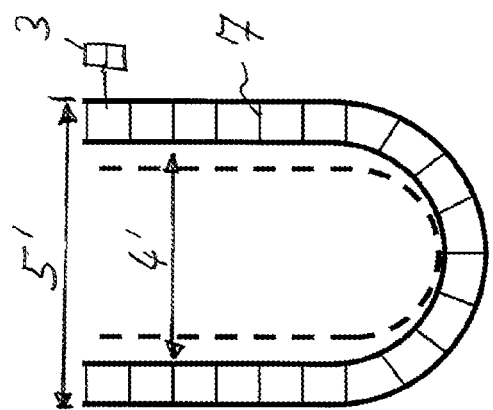
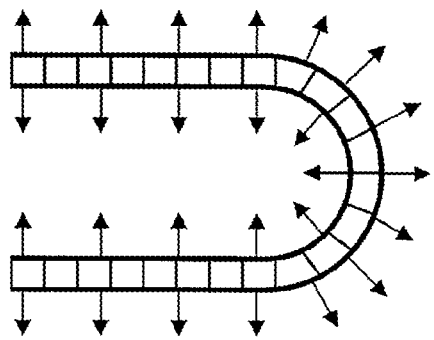
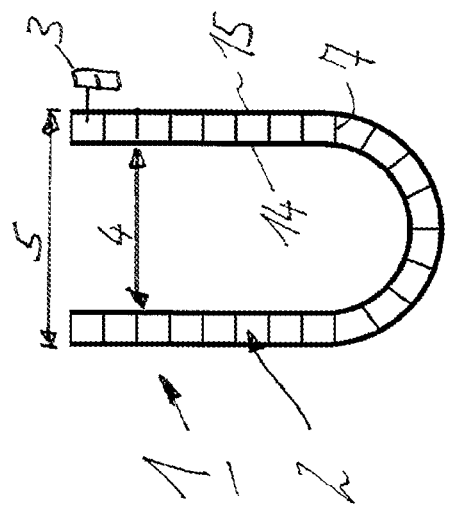
Fig. 1

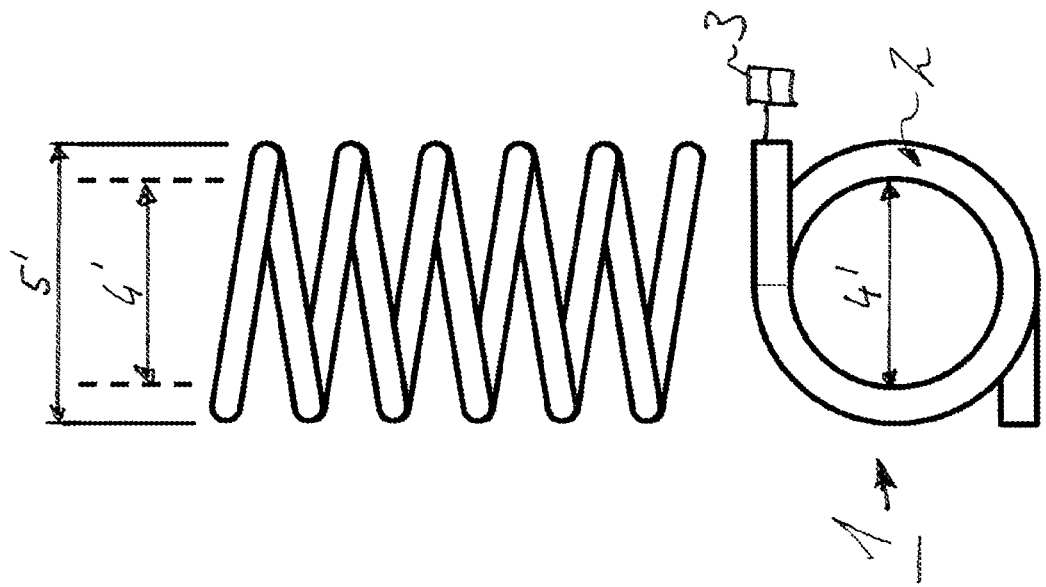
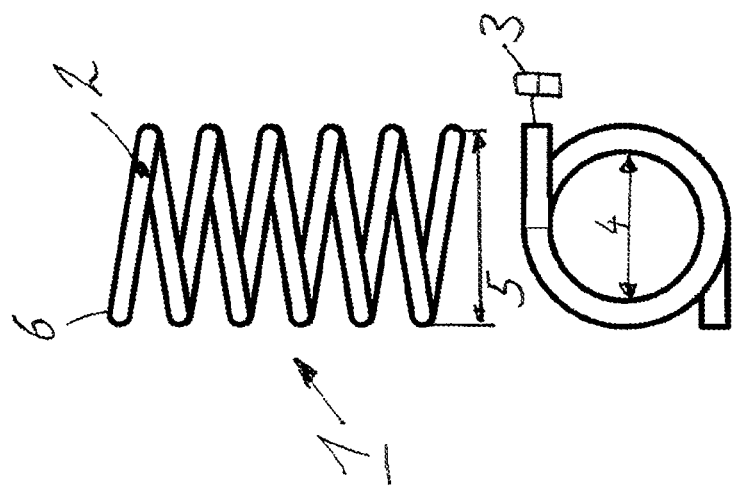

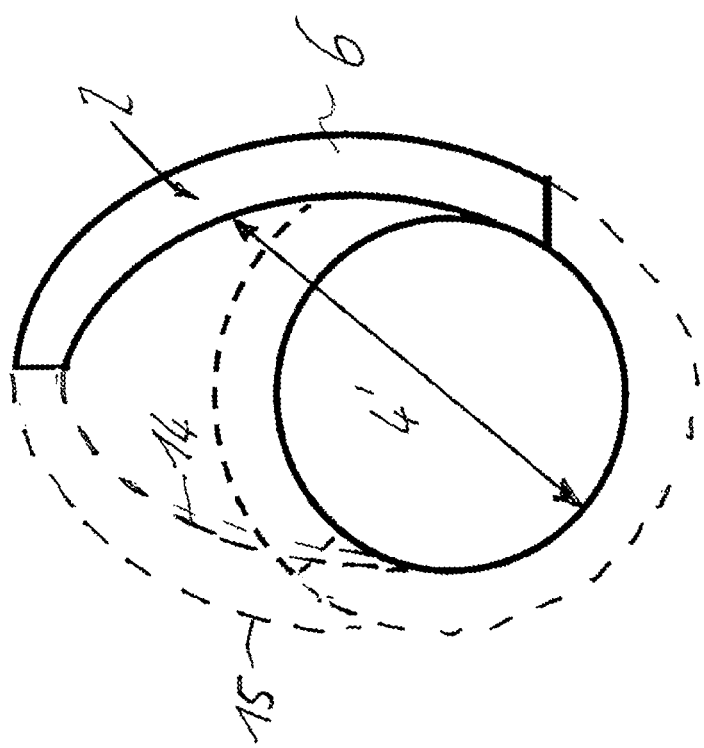
Fig. 3
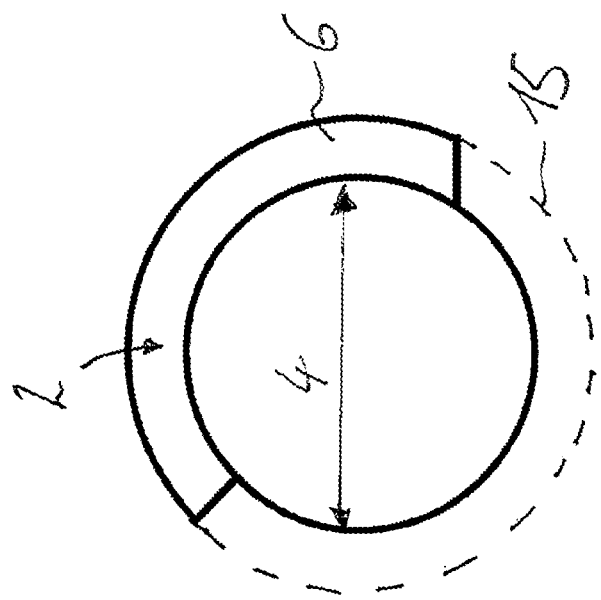

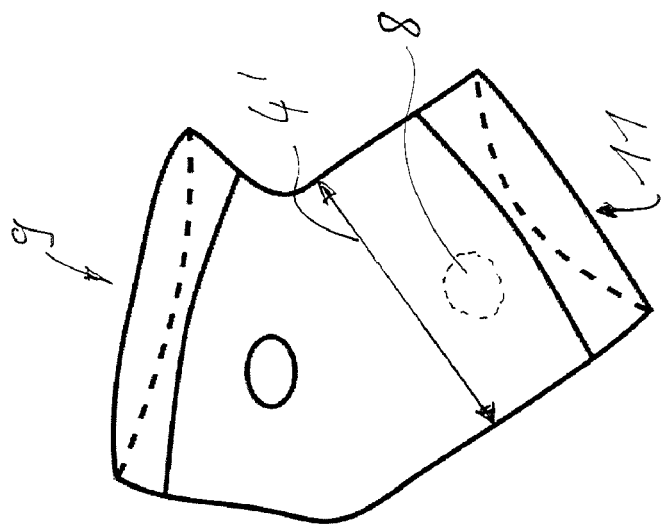
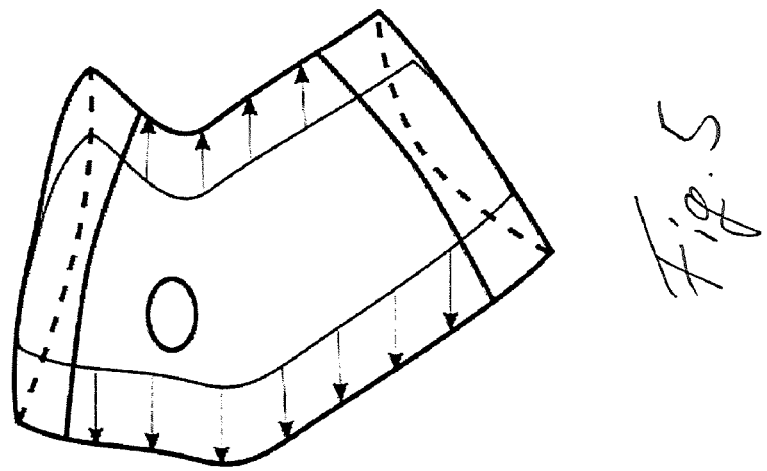
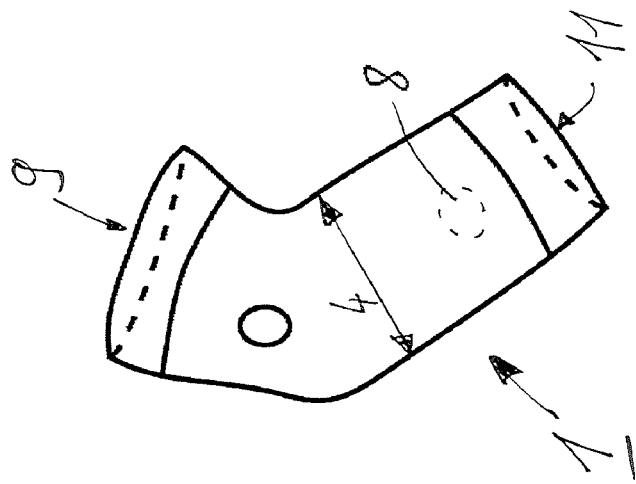
Fig. 5

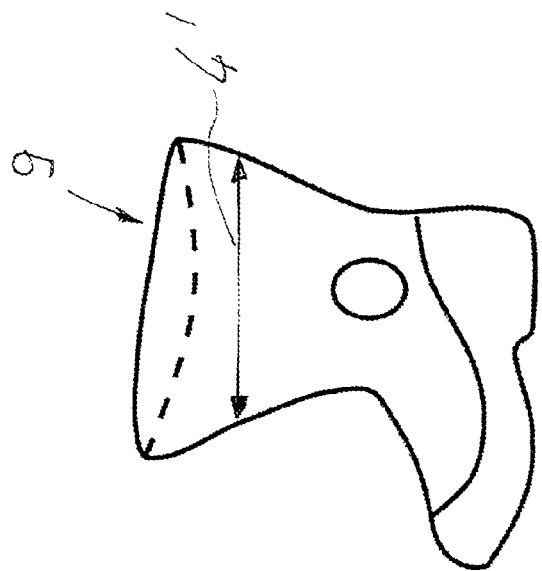
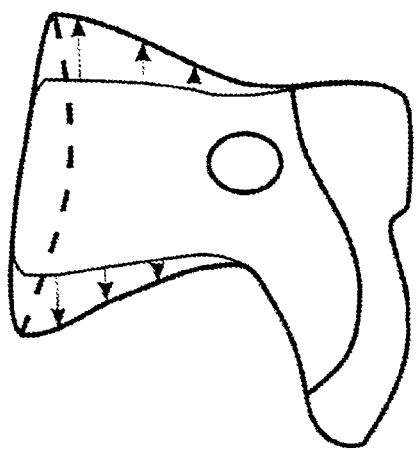
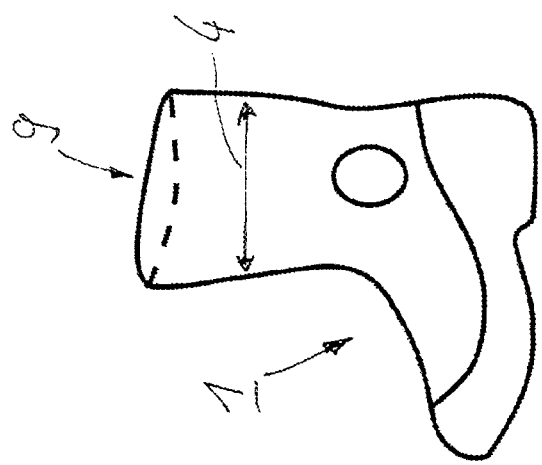
Fig. 6

ENVELOPING BODY

TECHNICAL FIELD

The invention relates to an enveloping body for at least partly enveloping a limb, comprising an enclosed volume and a connection for supplying fluid to the volume and discharging it from the volume, wherein the enveloping body defines an inner circumference and an outer circumference. The enveloping body is intended to bear either on a stump or on a limb.

BACKGROUND

Between a prosthesis socket and a limb stump, a liner is provided in order to cushion the stump, to compensate for irregularities in the socket surface and to produce a connection between the stump and the prosthesis socket, said liner being pulled on over the stump. The liner generally adheres to the skin surface of the stump and, at its distal end, can have locking elements, for example a pin that interacts with a corresponding mechanical locking device in the prosthesis socket. In the context of vacuum socket technology, a sealed-off volume can be formed between the liner and the prosthesis socket, from which volume air is withdrawn via a pump or a valve. The vacuum has the effect that the prosthesis socket is held on the prosthesis liner.

The prosthesis liners are generally made from an elastomer material, for example silicone, having a high degree of adherence to the stump. To put it on, the liner is rolled up, the distal and preferably closed end of the prosthesis liner is placed onto the stump end, and the liner is then unrolled over the stump. The liner generally has an internal diameter smaller than the external diameter of the stump, in order to permit a relatively secure fit on the stump.

A problem here is that the material has to be sufficiently stretched in order to be able to apply the prosthesis liner. This is difficult to do, particularly for patients who have further physical limitations.

U.S. Pat. No. 5,387,245 A discloses a prosthesis liner comprising an inner liner and an outer liner made of an elastomer material. The inner liner and the outer liner are adhesively bonded to each other, wherein, in order to form a bladder between the inner liner and the outer liner, one region is not adhesively bonded. A valve is assigned to the bladder and allows air to be introduced into the bladder or released, so as to be able to compensate for fluctuations in the volume of the stump.

In the prior art there are also bandages or cuffs which are placed around a limb in order to apply a circumferential pressure to the limb. Such bandages or cuffs are preferably produced from a woven fabric or a neoprene. These enveloping bodies, which have a proximal opening and a distal opening, likewise have to be stretched in order to fit them in place.

SUMMARY

The object of the present invention is to make available an enveloping body which is easy to apply and whose fit is individually adaptable to the user.

According to the invention, this object is achieved by an enveloping body. Advantageous embodiments and refinements of the invention are disclosed in the description and the figures.

In the enveloping body according to the invention for at least partly enveloping a limb, comprising an enclosed volume and a connection for supplying fluid to the volume and discharging it from the volume, wherein the enveloping body defines an inner circumference and an outer circumference, provision is made that the inner circumference of the enveloping body increases as the pressure of the volume increases. When fluid is released from the volume, the inner circumference of the enveloping body decreases on account of an elastic restoring force which is preferably applied by the material of the enveloping body. By means of a pressure increase within the enveloping body, it is thus possible to obtain a circumferential widening of the interior of the enveloping body, such that the enveloping body can be easily put on. Once the enveloping body is in the desired position, i.e. has been placed either around a stump or around a limb, the fluid can be released from the enclosed volume, as a result of which the internal pressure decreases and the inner circumference conforms and adapts to the contour of the stump or of the enclosed limb. The degree of the contact pressure can be varied through the choice of the internal pressure. The lower the internal pressure, the greater the contact pressure on the limb. The maximum contact pressure is determined by the material properties of the enveloping body and by the dimensions of the latter. The greater the underdimension of the enveloping body with a volume not subjected to pressure, the greater the pretensioning with respect to the stump or the limb.

In one embodiment of the invention, the enveloping body has an inner wall and an outer wall which enclose the volume that can be filled with fluid. The fluid used is preferably a compressive medium, in particular the ambient air. The inner wall and the outer wall can be connected to each other in a fluid-tight manner for example in their distal and proximal end regions, such that, for example in an embodiment as a liner, the volume has a sleeve-shaped configuration. The volume is then arranged in the region of the side wall which extends from a distal closed end region as far as the proximal access opening. In the case of a cuff, which preferably has a closed cross section, the volume preferably extends about the entire circumference. In an embodiment of the enveloping body as a shoe with a shank region, it may be the shank region alone that is provided with a volume in order to increase the inner circumference of the shank, or else the entire shoe together with the foot region, wherein the sole can be configured with a single wall or a double wall without volume, for example by adhesively bonding an inner part of the shoe to an outer part of the shoe or an inner shoe to an outer shoe in the sole region. The inner wall and the outer wall are preferably produced from the same material; they at least have the same elastic properties.

At least the inner wall of the enveloping body can be elastic; preferably the inner wall and the outer wall are both elastic in order to permit widening of both walls. There is also the possibility that the outer wall is elastic and the inner wall is only partially elastic or also made of a pleated or gathered non-elastic material. Non-elastic is understood as meaning materials whose length does not change, or does not appreciably change, under the pressures and forces customary in the field in question. In addition to a complete elastic configuration, for example by forming the respective wall entirely from an elastomer, it is also possible for elastic regions to be provided only in some areas in the inner wall and/or outer wall in order to permit an enlargement of the inner circumference of the enveloping body in the event of a pressure increase. Provision is likewise made that the inner wall and/or the outer wall of the enveloping body are foldable, such that an enlargement of the circumference is obtained by the unfolding of the respective wall. The folds are subjected to a restoring force such that, after a reduction of the internal pressure, a corresponding reduction of the inner circumference can also take place. The folds are configured in the manner of a concertina, for example. The inner wall and/or outer wall can thus be foldable and/or elastic.

Elements transmitting tensile force can be arranged between the inner wall and the outer wall, wherein the elements transmitting tensile force can be rigid under tension or elastic. Elements that are rigid under tension are understood as elements which, when the pressure within the volume increases, have no elongation or have less elongation than the inner wall and/or the outer wall. The elements transmitting tensile force can be configured as straps, webs or pins and can either be formed integrally with the walls or can be secured separately thereon.

A further possibility for widening the inner circumference of the enveloping body is that the latter has at least one hollow space routed at least partially circumferentially about the inner circumference, wherein the hollow space surrounds the fillable volume. On account of the curvature that is present in the initial state, the arrangement of the hollow space partially circumferentially about the inner circumference has the effect that, when the pressure in the hollow space increases, there is a tendency for the hollow space to straighten, such that a widening of the inner circumference takes place overall. Several hollow spaces routed partially circumferentially about the inner circumference can be arranged one after another along the longitudinal extent of the enveloping body. The hollow spaces can be configured in a common orientation or in alternating orientations or they can be arranged alternately in one orientation and the other about the inner circumference. If the hollow spaces are present only partially circumferentially, each hollow space or each hollow space portion can be supplied with the fluid via a common supply line, for example. Similarly, the fluid is withdrawn from the hollow spaces or hollow space portions jointly through this supply line. The hollow space can be circular, i.e. routed almost completely about the inner circumference. Furthermore, there is the possibility that the hollow space is routed helically about the inner circumference, in the manner of a helical spring or spiral spring, in which case the diameter of the walls increases and the inner circumference enlarges when the internal pressure within the hollow space increases.

The hollow space or the respective hollow space portion preferably has a hose-like configuration. If the hollow space is secured between an inner wall and an outer wall or is also just arranged on an inner wall or an outer wall, the hollow space itself does not need to have elastic restoring forces; the latter can instead be provided by the respective wall. The hollow space or hose can be secured to the inner wall and/or outer wall; it is likewise possible that the hollow space is located between the inner wall and the outer wall and is positioned within the enveloping body by the walls themselves. The hose-like hollow space is preferably configured as an elastic hose, wherein the elasticity in the hose diameter may be present in connection with the inner circumference surrounded by the hose, such that hose diameter and inner circumference increase when the pressure increases. It is likewise possible that the elasticity is effective substantially only in the inner circumference surrounded by the hose, i.e. the inner circumference increases in size when the pressure increases, without the hose diameter substantially changing.

The enveloping body can at least partially have an adhesive inner surface in order to ensure secure positioning of the applied enveloping body on the stump of the limb. Preferably, the volume extends over the entire axial extent of the enveloping body, either by the configuration of the volume between two walls or else by a corresponding arrangement of hollow bodies arranged axially one after another over the entire length or almost the entire length of the enveloping body.

The enveloping body is preferably configured as a prosthesis liner, bandage, cuff, item of clothing or shoe. In particular, the enveloping body serves as an orthopedic aid or orthopedic device, for example as an orthosis or prosthesis. It can be configured as a medical aid, for example as a compression sleeve for first aid, as a supporting means or splint or as an accessory for orthoses, prostheses or orthopedic devices or medical aids. It is moreover suitable as an item of clothing or part of an item of clothing, for example as a protective garment, a protector, a leisure garment, as an aid for pulling on socks, compression stockings or similar. Areas of use are in sports clothing and sports equipment, such as diving suits, and likewise in work clothing, e.g. clothing for fire fighters. In the embodiment as a prosthesis liner, the enveloping body serves as an interface between the stump and a prosthesis socket; in a bandage, for example, the enveloping body supports a joint region or assists the muscles and proprioception via a radially acting pressure applied from outside. In an embodiment as a shoe, a secure hold of the shoe on the foot can be ensured; if appropriate, a prosthetic foot can be secured directly to a stump or socket in the ankle region or lower leg region via a cuff. With regard to a use as a shoe or in a shoe, advantageous areas of use are in particular boots for motorcyclists and boots for firefighters. Further areas of use are insertion aids for helping elderly or physically impaired persons, rubber boots with a sealing lip, or leisure shoes.

BRIEF DESCRIPTION OF THE DRAWINGS

Illustrative embodiments of the invention are explained in more detail below with reference to the attached figures, in which:

FIG. 1 shows a schematic view of an enveloping body in the form of a prosthesis liner in two states;

FIG. 2 shows a schematic view of an enveloping body with a helical hollow body;

FIG. 3 shows a schematic view of the function of a hollow body with a partially circumferential hollow body;

FIG. 5 shows a schematic view of a bandage; and

FIG. 6 shows a schematic view of an enveloping body in the form of a shoe.

DETAILED DESCRIPTION

Figure 4:
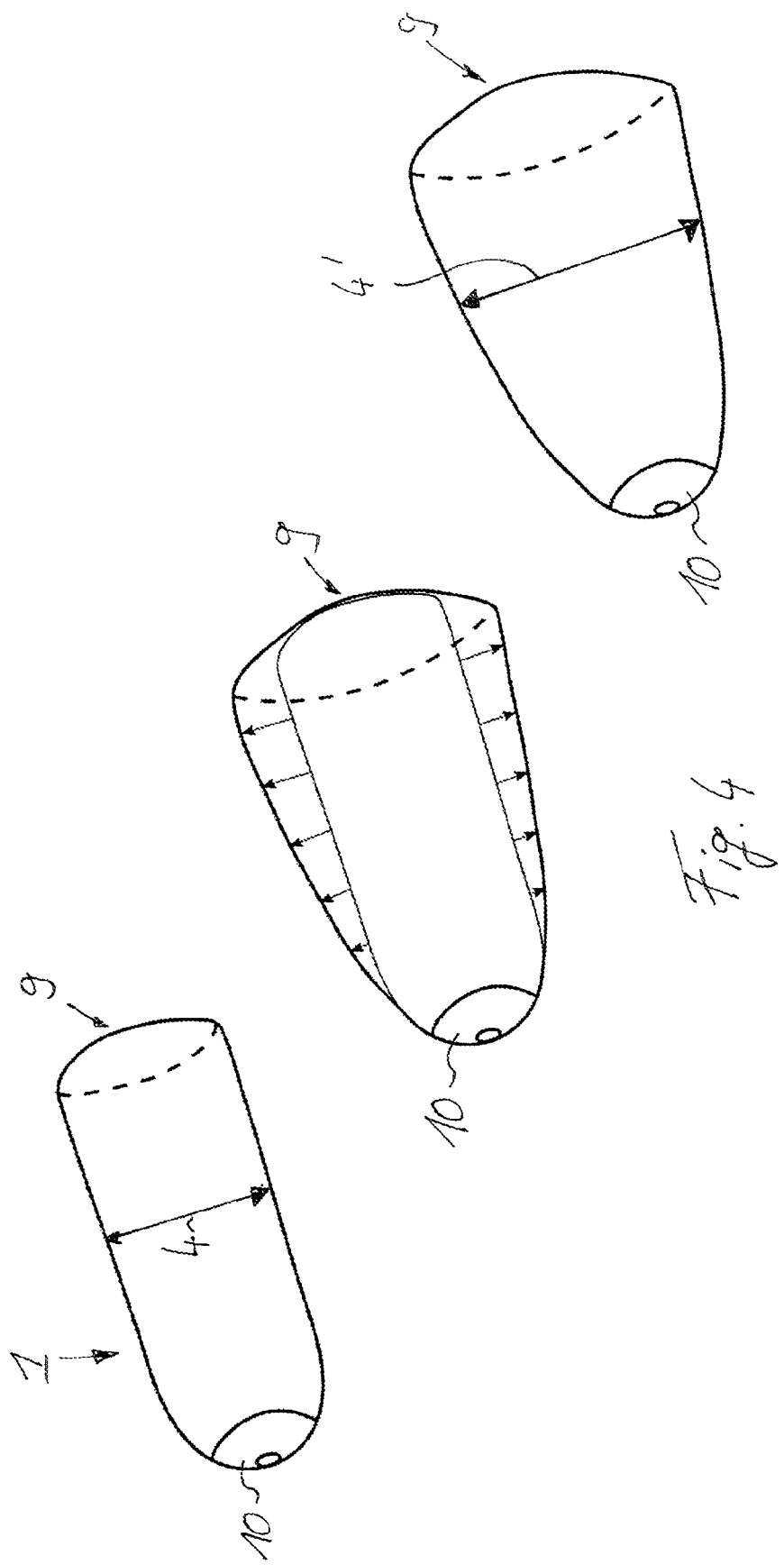
FIG. 4 shows a perspective view of an enveloping body as a prosthesis liner.

FIG. 1 shows a schematic view of an orthopedic enveloping body 1 in the form of a prosthesis liner as a basic implementation of the invention. The enveloping body 1 has an inner wall 14 and an outer wall 15, which between them enclose a volume 2. The enveloping body 1 is thus double-walled and has a connection 3 with a valve in order to fill the volume 2 between the inner wall 14 and the outer wall 15 with a fluid or to drain fluid from the volume 2. The fluid is preferably ambient air. A multiplicity of elements 7 for transmitting tensile force are formed between the inner wall 14 and the outer wall 15 and, in the illustrative embodiment shown, are configured as webs. Instead of the webs, there is also the possibility of providing straps, pins or also just connection points between the inner wall 14 and the outer wall 15. In the state when not filled with fluid, the inner wall 14 can bear on the outer wall 15.

The enveloping body 1 is U-shaped in longitudinal section, while it has a substantially circular, closed contour in the cross section perpendicular to the longitudinal extent of the enveloping body 1. In the unfilled state shown, an inner circumference 4 and an outer circumference 5 are thus present; the dimensions of the circumferences 4, 5 derive from the shape, size and material properties.

When fluid is introduced into the closed-off volume 2 via the connection 3, the pressure inside the volume 2 increases since both the inner wall 14 and the outer wall 15 are made of an elastic material, preferably an elastomer, or a combination of elastic portions and non-elastic portions. As a result of the increased internal pressure, corresponding forces act on the inner wall 14 and the outer wall 15; greater forces act on the outer wall 15 on account of the latter having a larger surface area. With identical material properties in terms of elongation, for example when the inner wall 14 and the outer wall 15 are made of the same material, greater deformation and elongation take place on account of the greater forces acting on the outer wall 15, which has the effect that the enveloping body as a whole is stretched out. This is shown on the right in the figure. In the state when subjected to pressure, the outer circumference 5' is increased compared to the view on the left. The inner circumference 4' is also increased by comparison with the initial state, which is indicated by the broken line, as also is the distance between the inner wall 14 and the outer wall 15.

Through the pressure applied via the valve and the access 3, it is possible to increase the internal diameter and thus also the circumference 4 of the receiving space of the enveloping body 1 for the limb or the stump, such that the stump (not shown) can be easily inserted. When the valve at the access 3 is opened, air escapes from the volume 2 on account of the elastic restoring forces that are made available by the inner wall 14 and the outer wall 15. The volume of the receiving space for the stump decreases, the inner wall 14 bears on the stump (not shown), and a secure fit of the enveloping body 1 on the stump is permitted. Depending on the degree of pressure reduction, a suitable pressing force of the inner wall 14 on the stump is obtained, wherein the maximum pressing force is obtained when the volume 2 is minimized.

FIG. 2 shows a variant of the invention in which, instead of a sleeve-like volume 2, a hose-like volume 2 is formed by a hose-shaped hollow space 6. The hollow space 6 has a helical or screw-shaped arrangement and, in the view on the left, is not filled with a pressure fluid and has a first inner circumference 4. The hollow space 6 is wound several times, such that the interior is completely surrounded several times.

In the view on the right, pressure fluid has been pumped into the volume 2. As a result of the increase in pressure, the hollow body 6 has a tendency to cancel or increase the curvature, resulting in an increased diameter and therefore an increase of the inner circumference 4 and of the outer circumference 5 of the enveloping body 1. The view on the right in FIG. 2 shows the increased inner circumference 4' and also the increased outer circumference 5'. The hollow space 6 in the form of the helix can form the enveloping body 1 as a tube. As an alternative to this, such a hollow space 6 can be arranged in for example a double-walled liner as per FIG. 1 or else can be equipped on the inner face and/or outer face with a substantially closed layer or wall, such that a smooth contact surface on the limb or the stump can be achieved or a smooth-walled closure on the outside. The hollow body 6 thus serves as an actuator for increasing the diameter and therefore for increasing the inner circumference 4 when the pressure increases, such that the enveloping body 1 can be easily applied in the state when subjected to pressure. When the internal pressure in the volume 2 decreases, the hollow space 6 contracts again to the initial position according to the view on the left, such that the enveloping body 6 bears around the stump or around the limb.

FIG. 3 shows a schematic view of an alternative embodiment in which, instead of a helical profile of the hollow space 6, the stump (not shown) or the limb (not shown) is surrounded by the hollow space 6 about only part of the circumference. Here too, the volume can be subjected to a variable internal pressure via a valve and a connection (not shown). An outer wall 15, which can optionally be arranged around the hollow space 6, is indicated by a broken line. Moreover, an inner wall 4 can be arranged at the hollow space 6. Several hollow spaces 6 can be arranged axially one after another, i.e. arranged perpendicularly with respect to the drawing plane. The hollow spaces 6 can be arranged mutually offset, in particular mutually offset in the circumferential direction, such that the effect that arises when the volume 2 is increased at the hollow space 6 can be obtained along the entire length in the axial direction.

The view on the right in FIG. 3 shows the position and shape of the hollow space 6 after the pressure increase. The hollow space 6 tends toward a straightening and thus increase in size of the radius of curvature, which results in the shape of the hollow space 6 as shown in the view on the right. This change of shape is accompanied by an increase in size of the inner circumference 4', the inner and outer walls 14, 15 optionally coupled to the hollow space 6 deform accordingly, such that an approximately elliptic or oval inner contour is obtained. If several hollow spaces 6 are arranged one after another in the axial direction, this results in an approximately circular inner and outer contour. If several finger-like hollow spaces 6 are provided which are spaced apart from one another in the axial direction along the longitudinal extent of the enveloping body 1, they can be supplied with the pressure fluid via a common supply line, such that, by actuation of just one valve, there is the possibility of widening the entire enveloping body 1 or of reducing its inner circumference 4.

FIG. 4 shows an embodiment of the enveloping body 1 in the form of a prosthesis liner with a proximal insertion opening 9 and a closed distal end region 10. A dimensionally stable cap and receiving devices for mechanical locking elements or the like can be arranged at the distal end region 10. In the view at the top, the prosthesis liner 1 has a first circumference 4. From the distal end region 10, a side wall extends substantially conically in the direction of the proximal access opening 9. The side wall or the side wall region has a double-walled configuration; the distal end region 10 is either formed as one layer, or the two layers of a double-walled prosthesis liner are bonded adhesively to each other or joined cohesively to each other. No pressure fluid can be introduced in the distal end region 10.

The middle view in FIG. 4 shows the acting forces when a pressure fluid is introduced into the hollow space formed in the side wall or into the volume enclosed between an inner liner and an outer liner. The view on the right shows the shape of the prosthesis liner 1 at an increased internal pressure in the volume. The inner circumference 4' is greater than the initial inner circumference 4; the access opening 9 of the prosthesis liner closed in the distal end region 10 is considerably larger than the original access opening 9. This makes placing the stump into the prosthesis liner 1 easier. After the stump end has made contact with the inner face of the distal end region 10, the valve at the connection 3 is opened, the air escapes, and the side wall of the prosthesis liner conforms to the stump.

An alternative embodiment of the invention is shown in FIG. 5, in which the enveloping body 1 is configured in the form of a pneumatically modifiable bandage. The bandage can be configured as a knee bandage and bridge a joint. It can alternatively be configured as an elbow bandage, a wrist bandage or an ankle bandage. An additional possibility is that the bandage is not configured to bridge a joint and instead can engage completely around the upper leg, upper arm, lower leg or forearm, for example. The cross section of the bandage is closed in the illustrative embodiment shown. The bandage 1 is double-walled along its entire length, between the proximal access opening 9 and the distal exit opening 11, and can have pressurized air applied to it via a connection (not shown). The application of pressurized air is shown in the middle view in FIG. 5, which illustrates how the bandage 1, from the initial state shown in the left-hand view, is converted to the end state shown in the right-hand view. The inner circumference 4' in the pressurized state according to the view on the right is greater than the initial circumference 4, such that the bandage can be easily applied. Compression takes place by release of pressurized air. Regions 8 of increased adhesiveness can be formed on the inner face of the bandage 1, such that the enveloping body 1 has an adherent coating at least partially on its inner face 8.

FIG. 6 shows a further variant of the invention, in which the enveloping body 1 is configured as a pneumatically operated shoe or boot. The shank region of the enveloping body 1, extending above the natural ankle joint, has a double-walled configuration and forms a sleeve-like volume that can be filled with pressurized air. The filling process is shown in the middle view, while the view on the right shows how the proximal access opening 9 is considerably increased in size compared to the initial extent. The inner circumference 4' is likewise increased in relation to the original inner circumference 4, such that insertion into the shoe or boot 1 is made much easier. After insertion, the pressure in the volume can be reduced, as a result of which the shank conforms to the lower leg or below-knee stump or also a below-knee socket.

The invention claimed is:

1. An enveloping body for at least partly enveloping a limb, comprising:
   an inner wall and an outer wall that define an enclosed volume;
   elements attached to the inner wall and the outer wall within the enclosed volume to transmit a tensile force;
   a connection for supplying fluid to the enclosed volume and discharging fluid from the volume to change a pressure of the volume; and
   a tubular construction having a closed cross-section, an inner circumference, and an outer circumference, wherein the inner circumference of the enveloping body increases as the pressure of the volume increases, wherein the inner circumference of the enveloping body defines a continuous surface that defines the closed cross-section, and wherein the inner circumference is configured to exert a contact pressure on the limb and the contact pressure increases as the pressure of the volume decreases.

2. The enveloping body as claimed in claim 1, wherein at least one of the inner wall and the outer wall is at least one of foldable and elastic.

3. The enveloping body as claimed in claim 1, wherein the elements are rigid under tension or elastic.

4. The enveloping body as claimed in claim 1, wherein the enveloping body has a hollow space routed at least partially circumferentially about the inner circumference.

5. The enveloping body as claimed in claim 4, wherein the hollow space is routed in an at least partial circular shape or helical shape about the inner circumference.

6. The enveloping body as claimed in claim 4, wherein the hollow space has a hose-like configuration.

7. The enveloping body as claimed in claim 6, wherein the hollow space is configured as an elastic hose.

8. The enveloping body as claimed in claim 4, wherein the hollow space bears on a wall or is arranged between an inner wall and an outer wall.

9. The enveloping body as claimed in claim 1, wherein the enveloping body has an at least partially adhesive inner surface.

10. The enveloping body as claimed in claim 1, wherein the enveloping body is configured as a prosthesis liner, bandage, cuff, item of clothing or shoe.

11. An enveloping body for at least partly enveloping a limb, comprising:
    an enclosed volume;
    an inner wall and an outer wall, which enclose the volume;
    a connection for supplying fluid to the enclosed volume and discharging fluid from the volume to change a pressure of the volume;
    a tubular construction having a closed cross-section, an inner circumference, an outer circumference, wherein the inner circumference of the enveloping body increases as the pressure of the volume increases, wherein the inner circumference of the enveloping body defines a continuous surface that defines the closed cross-section, and wherein the inner wall is configured to exert a contact pressure on the limb and the contact pressure increases as the pressure of the volume decreases; and
    elements arranged between and connected to the inner wall and the outer wall within the enclosed volume to transmit tensile force, wherein an elongation of the elements is less than an elongation of the inner wall and the outer wall when the pressure of the volume increases.

12. The enveloping body as claimed in claim 11, wherein at least one of the inner wall and the outer wall is at least one of foldable and elastic.

13. The enveloping body as claimed in claim 11, wherein the elements are rigid under tension or elastic.

14. The enveloping body as claimed in claim 11, wherein the enveloping body has a hollow space routed at least partially circumferentially about the inner circumference.

15. The enveloping body as claimed in claim 14, wherein the hollow space is routed in an at least partial circular shape or helical shape about the inner circumference.

16. The enveloping body as claimed in claim 14, wherein the hollow space has a hose-like configuration.

17. The enveloping body as claimed in claim 16, wherein the hollow body is configured as an elastic hose.

18. The enveloping body as claimed in claim 11, wherein the elements are configured as straps, webs, or pins, and are formed integrally with the inner and outer walls or connected separately to the inner and outer walls.

* * * * *